United States Patent [19]

Moore

[11] 4,130,666

[45] Dec. 19, 1978

[54] ANTI-INFLAMMATORY METHOD

[75] Inventor: George G. I. Moore, Birchwood, Minn.

[73] Assignee: Riker Laboratories, Inc., Northridge, Calif.

[21] Appl. No.: 894,101

[22] Filed: Apr. 6, 1978

Related U.S. Application Data

[63] Continuation of Ser. No. 797,138, May 16, 1977, abandoned.

[51] Int. Cl.$^2$ .............................................. A61K 31/12
[52] U.S. Cl. ....................................................... 424/331
[58] Field of Search ......................................... 424/331

[56] References Cited

U.S. PATENT DOCUMENTS

| | | | |
|---|---|---|---|
| 3,592,931 | 7/1971 | Duennenberger et al. | 424/331 |
| 3,711,554 | 1/1973 | Engelhardt | 260/591 |
| 3,932,324 | 1/1976 | Stretanski | 260/23 H |
| 3,972,927 | 8/1976 | Susi et al. | 260/559 R |
| 3,992,434 | 11/1976 | Appelt et al. | 260/473 S |

OTHER PUBLICATIONS

J. Am. Chem. Soc., 95: 4698 (1973).
J. Org. Chem., 33: 1245 (1968).
J. Am. Chem. Soc., 79: 5019 (1957).

*Primary Examiner*—Stanley J. Friedman
*Attorney, Agent, or Firm*—Cruzan Alexander; Donald M. Sell; Donald C. Gipple

[57] ABSTRACT

Compounds in which 2,6-di(t-butyl)phenol is substituted in the 4 position by an acyl group have valuable pharmacological activity as anti-inflammatory agents.

7 Claims, No Drawings

ANTI-INFLAMMATORY METHOD

This is a continuation of application Ser. No. 797,138 filed May 16, 1977 now abandoned.

BACKGROUND OF THE INVENTION

This invention relates to the use of 2,6-di(t-butyl)-phenols substituted in the 4 position by an acyl group as anti-inflammatory agents.

Compounds in which 2,6-di(t-butyl)phenol is substituted in the 4 position by an acyl group are known to the art as polymer stabilizers and/or polymer antioxidants (see, for example, German Offenlugungschrift No. 1,811,322). No physiological use of such compounds has been reported, however.

DETAILED DESCRIPTION OF THE INVENTION

Specifically the invention relates to a method for combatting inflammatory processes in mannalian animals which comprises administering thereto an effective dose, less than the toxic amount, of a compound of the formula:

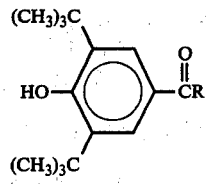

wherein R is cycloalkyl of 3 to 6 carbon atoms or ethyl, n-propyl or n-butyl. The invention also relates to anti-inflammatory compositions comprising one or more 2,6-di(t-butyl)phenols substituted in the 4 position by an acyl group together with a suitable pharmaceutical extending medium. Acyl groups of the invention are cycloalkanoyl or alkanoly groups as defined hereinabove.

In addition to their anti-inflammatory activity, some of these compounds are also analgesic and antipyretic agents and some have mild immunosuppressant activity.

In order to determine and assess pharmacological activity, testing in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response (the rat foot edema test). The compounds (I above) have also been found to inhibit the enzyme prostaglandin synthetase and some of them are quite active when administered dermally. Such topical activity has been measured by means of the guinea pig erythema test and by a contact sensitivity test. Anti-inflammatory activity may also be detected by other assays known to the art such as the cotton pellet granuloma test and the adjuvant arthritis test. The analgesic activity has been observed in standard test methods such as the phenylquinone writhing (mouse) and Randall-Selitto (rat) tests.

Leading references to the rat foot edema method are:
(1) Adamkiewicz et al, Canad. J. Biochem. Physio. 33:332, 1955;
(2) Selye, Brit. Med. J. 2:1129, 1949; and
(3) Winter, Proc. Exper. Biol. Med. 111:544, 1962.

The edema test is performed on adult female rats. One group of 10 rats serves as non-medicated controls, while another group of 10 rats receives the test compound at various times prior to the induction of the edema, usually 15 minutes, 1 hour and/or 18 hours. The test compound is administered orally as a suspension in 4 percent aqueous solution of acacia. Edema is induced by the plantar injection of 0.5 percent carrageenin (0.1 ml/foot) into the right hind foot. The left hind foot receives a like volume of 0.9 percent saline solution. One hour later, the volume of each hind foot is determined plethysmographically. The edema is expressed as the increase in the volume of the edemogen-injected foot (volume of the "edemogen foot" less the volume of the "saline foot"). The percent inhibition is calculated by dividing the mean increase in the edema of the edemogen foot of the medicated group by the mean increase in the non-medicated group, multiplied by 100. An active dose is that giving a statistically significant inhibition of the induced edema, usually in the range of about 25–35 percent inhibition.

The compounds are preferably administered orally as anti-inflammatory agents but other known methods of administration are contemplated as well, e.g. dermatomucosally (for example dermally, rectally and the like) and parenterally, for example by subcutaneous injection, intramuscular injection, intra-articular injection, intravenous injection and the like. Ocular administration is also included. Dosages ordinarily fall within the range of about 1 to 500 mg/kg of body weight of the mammal to be treated although oral dosages are not usually above 100 mg/kg. Suitable forms for oral administration include liquids (such as 4 percent acacia and polyethylene glycol solutions), tablets (which may contain anhydrous lactose, microcrystalline cellulose, modified starch, calcium stearate and talc, as well as other conventional compounding agents together with the active anti-inflammatory agents), solid suspensions and capsules. Suitable carriers for topical application include creams, gels, tapes and the like. Liquid formulations, such as solutions or suspensions of the active ingredient in inert carriers, are contemplated for dosage by injection.

The compounds which are presently preferred for use in the process of the invention (due to their high oral activity) are:

3',5'-di-t-butyl-4'-hydroxyvalerophenone and
3',5'-di-t-butyl-4'-hydroxybutyrophenone.

The compounds of the invention are prepared using the methods described in the prior art; see, for example, U.S. Pat. No. 3,711,554, issued Jan. 16, 1973, and United States Patent 2,903,487.

The following examples, which are not intended to in any way limit the scope of the invention, are illustrative thereof.

EXAMPLE 1

To a solution of 0.10 mole (11.9 g.) of cyclobutanecarbonyl chloride in 200 ml. of dichloroethane is added 0.11 mole (20.9 g.) of titanium tetrachloride, then 0.10 mole (20.6 g.) of 2,6-di(t-butyl)phenol in dichloroethane. After stirring for a total of 15 to 30 minutes the mixture is poured into 10 percent hydrochloric acid and dried over anhydrous magnesium sulfate. Evaporation provides a solid product which is washed thoroughly with petroleum ether and recrystallized (treated with decolorizing charcoal) from a hexane-benzene mixture. The white solid is 3,5-di(t-butyl)-

4-hydroxyphenyl cyclobutyl ketone, m.p. 140°–141.5° C.

| Analysis: | % C | % H |
|---|---|---|
| Calculated for $C_{19}H_{28}O_2$: | 79.1, | 9.8 |
| Found: | 79.1, | 9.9. |

EXAMPLE 2

Reacting cyclopropanecarbonyl chloride with 2,6-di(t-butyl)phenol by the method of Example 1, white, solid 3,5-di(t-butyl)-4-hydroxyphenyl cyclopropyl ketone, m.p. 140.5°–142.5° C. is obtained.

| Analysis: | % C | % H |
|---|---|---|
| Calculated for $C_{18}H_{26}O_2$: | 78.8, | 9.6 |
| Found: | 78.8, | 9.7. |

The following additional compounds of the invention are also prepared by the method of Example 1:

3,5-di(t-butyl)-4-hydroxyvalerophenone, m.p. 85.5°–87° C.

3,5-di(t-butyl)-4-hydroxyphenyl cyclopentyl ketone, m.p. 126°–128° C., 3,5-di(t-butyl)-4-hydroxybutyrophenone, m.p. 91°–93° C., 3,5-di(t-butyl)-4-hydroxypropiophenone, m.p. 135°–136.5° C. and 3,5-di(t-butyl)-4-hydroxyphenyl cyclohexyl ketone, m.p. 125°–127° C.

Several compounds of the invention are tested in the rat foot edema test at a dose of 100 mg/kg p.o. and are found to have statistically significant activity. They are:

3,5-di(t-butyl)-4-hydroxyvalerophenone,
3,5-di(t-butyl)-4-hydroxyphenyl cyclobutyl ketone,
3,5-di(t-butyl)-4-hydroxyphenyl cyclopentyl ketone,
3,5-di(t-butyl)-4-hydroxybutyrophenone,
3,5-di(t-butyl)-4-hydroxypropiophenone, and
3,5-di(t-butyl)-4-hydroxyphenyl cyclohexyl ketone.

What is claimed is:

1. A method for combatting inflammatory processes in a mammal which comprises administering an effective dose less than the toxic amount of a compound of the formula:

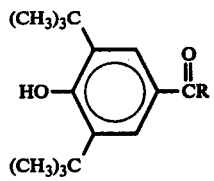

wherein R is cycloalkyl of 3 to 6 carbon atoms, ethyl, n-propyl or n-butyl to said mammal.

2. A method according to claim 1 wherein R is n-propyl.

3. A method according to claim 1 wherein R is n-butyl.

4. A method according to claim 1 wherein R is cyclobutyl.

5. A method according to claim 1 wherein R is cyclopentyl.

6. A method according to claim 1 wherein R is ethyl.

7. A method according to claim 1 wherein R is cyclohexyl.